United States Patent
Chao (12)

(10) Patent No.: US 6,368,825 B1
(45) Date of Patent: Apr. 9, 2002

(54) BACULOVIRUS CONTAINING MINIMAL CMV PROMOTER

(75) Inventor: Yu-Chan Chao, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/364,223

(22) Filed: Jul. 29, 1999

Related U.S. Application Data

(60) Provisional application No. 60/095,999, filed on Aug. 10, 1998.

(51) Int. Cl.[7] .................. C12N 15/866; C12N 15/63
(52) U.S. Cl. ................... 435/69.1; 435/320.1; 435/455; 435/456; 435/348; 435/235.1
(58) Field of Search ............... 435/320.1, 455, 435/456, 69.1, 348, 235.1

(56) References Cited

U.S. PATENT DOCUMENTS

| | | | |
|---|---|---|---|
| 5,731,182 A | 3/1998 | Boyce | 435/183 |
| 6,004,941 A | * 12/1999 | Bujard et al. | 514/44 |

OTHER PUBLICATIONS

Harding, T. C. et al., "Tetracycline–Regulated Transgene Expression in Hippocampal Neurones Following Transfection with Adenoviral Vectors," Journal of Neurochemistry, vol. 69, No. 6, pp. 2620–2623, 1997.

Gossen, Manfred et al., "Tight control of gene expression in mammalian cells by tetracycline–responsive promoters," Proc. Natl. Acad. Sci., vol. 89, pp. 5547–5551, 1992.

Ho, Dora Y. et al., "Inducible gene expression from defective herpes simplex virus vectors using the tetracycline–responsive promoter system," Molecular Brain Research, vol. 41, pp. 200–209, 1996.

Paulus, Werner et al., "Self–Contained, Tetracycline–Regulated Retroviral Vector System for Gene Delivery to Mammalian Cells," vol. 70, No. 1, pp. 62–67, 1996.

Pfeifer, Tom A. et al., "Baculovirus immediate–early promoter–mediated expression of the Zeocin™ resistance gene for as a dominant selectable marker . . . ," vol. 188, pp. 183–190, 1997.

* cited by examiner

Primary Examiner—David Guzo
(74) Attorney, Agent, or Firm—Fish & Richardson P.C.

(57) ABSTRACT

A recombinant baculovirus having a genomic DNA molecule which includes a CMV immediate-early promoter sequence and a sequence encoding an RNA. The expression of the RNA is driven by the CMV promoter sequence, which has deleted part of the sequences present in the full-length CMV promoter sequence.

9 Claims, No Drawings

BACULOVIRUS CONTAINING MINIMAL CMV PROMOTER

CROSS REFERENCE TO RELATED APPLICATIONS

This application claims priority from U.S. Provisional Application Ser. No. 60/095,999, filed Aug. 10, 1998.

BACKGROUND OF THE INVENTION

The baculoviruses are a family of DNA viruses which primarily infect insects of the order Lepidoptera. Baculovirus genomes are double-stranded DNA molecules, generally about 80–230 kb in length.

Baculoviruses are able to express large quantities of non-baculovirus proteins driven by the endogenous polyhedrin and p10 promoters, both of which are strongly active during the late stage of the virus life cycle. However, for some proteins, expression earlier in the baculovirus life cycle may be appropriate and preferred. For example, it may be desirable to drive expression of a glycoprotein earlier in the virus life cycle since, by the late stage of the virus life cycle, post-translational glycosylation is at least somewhat impaired.

SUMMARY OF THE INVENTION

The invention is based on the discovery that a minimal cytomegalovirus (CMV) immediate-early promoter can efficiently drive expression of a gene in a baculovirus vector. Because the CMV promoter is not regulated through the virus life cycle, this discovery allows the construction of a recombinant baculovirus containing minimal CMV promoter which is capable of high-level expression of a RNA or protein in the early stage, as well as the late stage, of the virus life cycle.

Accordingly, the invention features a baculovirus having a genome which includes a CMV promoter sequence and a sequence encoding an RNA (e.g., a non-baculovirus RNA). The expression of the RNA (e.g., a mRNA encoding a non-baculovirus protein) is driven by a minimal CMV promoter sequence (e.g., SEQ ID NO:1). Examples of minimal CMV promoter sequences include those that are free of SEQ ID NO:2, an upstream sequence often included in full-length CMV promoter sequences but absent in minimal CMV promoter sequences. These sequences are shown below.

A CMV minimal promoter sequence:

taggcgtgtacggtgggaggic-
tatataagcagagctcgtttagtgaaccgtcagatcac tagaagctttat-
tgcggtagtttatcacagttaaattgctaacgcagtcag (SEQ ID NO:1)

A sequence deleted from a full length CMV promoter:

tcaatattggccattagccatattat-
tcattggttatatagcataaatcaatattggcta ttggccattgcatacgttg-
tatctatatcataatatgtacatttatattggctcatgtcc aatatgaccgccat-
gttggcattgattattgactagttattaatagtaatcaattacggg
gtcattagttcatagcccatatatg-
gagttccgcgttacataacttacggtaaatggccc gcctggctgaccgc-
ccaacgaccccgcccattgacgtcaataatgacgtatgttcccat
agtaacgccaatagggactttccat-
tgacgtcaatgggtggagtatttacggtaaactgc ccacttggcagtacat-
caagtgtatcatatgccaagtccgcccccctattgacgtcaatga cgg-
taaatggcccgcctggcattatgcccagtacatgaccttacgggactttcctacttg
gcagtacatctacgtattagtcatcgc-
tattaccatggtgatgcggttttggcagtacac caatgggcgtggatgcg-
gtttgactcacggggatttccaagtctccaccccattgacgt caatgg-
gagtttgttttggcaccaaaatcaacgggactttccaaaatgtcgtaataaccc
cgccccgttgacgcaaatgggcgg (SEQ ID NO:2)

In the naturally occurring CMV genome, the CMV minimal promoter sequence (SEQ ID NO:1) is immediately downstream of the sequence deleted from the full length CMV promoter sequence (SEQ ID NO:2).

When a CMV promoter sequence is said to be free of SEQ ID NO:2, it means that the promoter sequence does not contain the complete nucleotide sequence of SEQ ID NO:2. Thus, the promoter sequence can contain a fragment of SEQ ID NO:2 and still be considered free of SEQ ID NO:2. Typically, a suitable CMV promoter sequence in the baculoviruses of the invention has a substantial deletion within SEQ ID NO:2 (e.g., at least 25, 50, 100, or 200 nucleotides deleted). Suitable CMV promoters can even contain a single nucleotide deletion of SEQ ID NO:2 and still be considered free of SEQ ID NO:2.

A CMV promoter sequence is any sequence derived from, but not necessarily identical to, a naturally occurring cytomegalovirus which is capable of driving RNA transcription in the context of a baculovirus genome. A non-baculovirus RNA or protein is any RNA or protein which is not encoded by the genome of a naturally occurring baculovirus, although a portion of a non-baculovirus RNA or protein can include a baculovirus sequence. For example, the non-baculovirus protein can be a fusion protein formed from a baculovirus protein and a human protein. The non-baculovirus protein can also be a detectable protein, such as luciferase, or an insect toxin that can augment the use of a baculovirus as a live biopesticide. Detectable proteins can exhibit enzymatic, radioactive, chromogenic, fluorescent, or luminescent properties.

The invention also includes a method of expressing a non-baculovirus RNA or protein in an insect cell by infecting the insect cell with a baculovirus of the invention.

The baculoviruses and methods of the invention provide life-cycle independent, high level expression of foreign RNAs and proteins (including recombinant baculovirus RNAs or proteins which are driven by a minimal CMV promoter). For example, an RNA encoding a biopesticide protein can be encoded by a sequence in a recombinant baculovirus. This baculovirus can then be used to control insect pest populations by natural infection.

Other features or advantages of the present invention will be apparent from the following detailed description, and also from the claims.

DETAILED DESCRIPTION OF THE INVENTION

The invention relates to a new baculovirus containing a minimal CMV promoter sequence which drives expression of an RNA or a protein. A minimal CMV promoter sequence is a functional CMV promoter that is free of SEQ ID NO:2 (see above), which is a sequence deleted from the full CMV immediate-early promoter sequence. An example of a minimal promoter sequence is SEQ ID NO:1 (see above).

Standard procedures for cloning baculoviruses having various foreign genetic elements are well known in the art.

Procedures for introducing recombinant baculoviruses into insects or cells thereof are also well known. See, e.g., Pfeifer et al., Gene 188:183–190, 1997; and Clem et al., J Virol 68:6759–6762, 1994.

Without further elaboration, it is believed that one skilled in the art can, based on the above disclosure and the description below, utilize the present invention to its fullest extent. The following example is to be construed as merely illustrative of how one skilled in the art can practice the invention and are not limitative of the remainder of the disclosure in any way. Any publications cited in this disclosure are hereby incorporated by reference.

The experimental procedures and recombinant plasmids and viruses used in the description below are first discussed.

To generate recombinant *Autographa californica* multiple nuclear polyhedrosis viruses (AcMNPVs), DNA encoding firefly luciferase and various promoters were cloned into the transfer vector pAcUW21 (PharMingen) which contains a complete polyhedrin gene and a p10 promoter for foreign gene expression (Roelvink et al., J Gen Virol 73:1481–1489, 1992; Vlak et al., Virology 179:312–320, 1990; and Weyer et al., J Gen Virol 71:1525–1534, 1990). The minimal CMV (CMVmin) promoter and TRE-CMVmin promoter are described in Gossen et al., Proc Natl Acad Sci USA 89:5547–5551, 1992. The CMVmin promoter encompasses the sequence between +75 and −53 of the CMV promoter. The TRE-CMVmin promoter contains seven copies of the 42-bp tetO sequence derived from operator O2 of Tn10 fused to the CMVmin promoter (Gossen et al., supra). The coding region of a luciferase gene, encompassing +30 of the transcription start site to the stop codon of firefly luciferase gene (Wet et al., Mol Cell Biol 7:725–737, 1987), was driven by a CMVmin promoter. A TRE-CMVmin promoter was derived from plasmid PTRE-Luc (ClonTech) and separately inserted into pAcUW21 to replace the p10 promoter originally located in this plasmid. The resulting plasmids were named pAPcmL and pAPtcmL, respectively. The luciferase coding sequence from the PTRE-Luc plasmid (from position 507 to 2187 bp, ClonTech) was also cloned into pAcUW21 under the control of the p10 promoter of AcMNPV in the plasmid pAcUW21, and the resulting plasmid was named pAP10L. The full-length CMV promoter derived from pTet-Off (from position 68 to 673 bp, ClonTech) together with the luciferase coding region derived from pTRE-Luc (from position 507 to 2187 bp, ClonTech), were inserted into pAcUW21 in replace of the p10 promoter, and the resulting plasmid was named pAPcL.

The coding region of the transactivator protein tTA from plasmid pTet-Off (ClonTech) was cloned into pAcUW21 under control of the p10 promoter, and the resulting plasmid was named pAP10T. The coding sequence of the enhanced green fluorescent protein (EGFP) from the pEGFP-1 plasmid (ClonTech) was cloned into pAcUW21 and placed under the control of the p10 promoter, and the resulting plasmid was named pAP10E. The luciferase coding sequence in the pAPtcmL plasmid was replaced with the EGFP coding sequence, and the resulting construct, in which the EGFP coding region was placed under the control of TRE-CMVmin promoter, was named pAPtcmE.

Plasmids pAPcL, pAP10L, pAPcmL, and pAPtcmL were cotransfected with vAcRP23.LacZ (PharMingen), a linearized genomic DNA of AcMNPV, into Sf21 cells using Lipofectin (Life Technologies). The resultant recombinant viruses contained a luciferase gene under the control of a full-length CMV promoter, a CMVmin promoter, a TRE-CMVmin promoter, and a p10 promoter. Each of these viruses were named vAPcL, vAPcmL, vAPtcmL, and vAP10L, respectively. The pAPtcmE and pAP10E plasmids were cotransfected with vAcRP23.LacZ. The resultant recombinant viruses containing the EGFP gene under the control of the TRE-CMVmin promoter and the p10 promoter were named vAPtcmE and vAP10E, respectively. The pAP10T was cotransfected with vAcRP23.LacZ, and the resultant recombinant virus containing the tTA gene under control of the p10 promoter was named vAP10T. All of these recombinant viruses were purified by three rounds of end point dilution and identified both by the presence of occlusions and luciferase, EGFP, or tTA expression.

Sf21 cells ($2 \times 10^5$) were washed twice with PBS and lysed for the indicated time in buffer (300 $\mu$l) containing 100 mM potassium phosphate (pH 7.8), 0.2% Triton X-100, and 2 mM β-mercaptoethanol. The cell lysate (50 $\mu$l) was incubated with reaction buffer (180 $\mu$l) containing 25 mM phosphate buffer (pH 7.8), 4 mM EGTA, 15 mM MgSO$_4$, 1 mM dithiothreitol, and 0.2 mM ATP. Afterwards, 50 $\mu$l of 0.2 mM luciferin (Promega) solution was auto-injected, and relative light units (RLU/10 seconds) were measured using a luminometer (Berthold, Lumat LB 9501). The results were plotted as the average luciferase activities versus time of infection from triplicate assays of three independent experiments.

A CytoFluor 2300/2350 fluorescence measurement system (Millipore) was used to quantify soluble EGFP fluorescence. Sf21 cells ($2 \times 10^5$) were twice washed with PBS buffer and lysed for the indicated times in buffer (300 $\mu$l) containing 100 mM potassium phosphate (pH 7.8), 0.2% Triton X-100, and 2 mM β-mercaptoethanol. Cell lysates (50 $\mu$l) were transferred to 96-well plates (Falcon) prior to EGFP fluorescence detection using a CytoFluor plate reader equipped with a 485/20 nm excitation filter and a 530/25 nm emission filter. The CytoFluor 2300/2350 fluorescence measurement system could quantify EGFP fluorescence linearly over a range of 0.1 to 100 $\mu$g/ml. The results were plotted as the average EGFP fluorescence versus time after infection, from triplicate assays of three independent experiments.

For immunoblotting analysis, proteins were fractionated by 12% SDS/PAGE and then transferred to a Hyperbond C membrane (Amersham). The membrane was blocked with Tris-buffer saline (TTBS; 100 mM Tris (pH 7.4), 100 mM NaCl, and 0.2% Tween-20) containing 3% non-dairy creamer at room temperature for one hour. The membrane was then incubated with primary antibody (either anti-luciferase antibody [Cortex Biochem] or anti-EGPF antibody [ClonTech]) in TTBS overnight at 4° C. Horseradish peroxidase (HRP)-conjugated secondary antibody was then added to the membrane, which was then incubated for one hour at room temperature. HRP was detected by an enhanced chemiluminescence kit (ECL; Amersham) following the protocol provided by the manufacturer.

The experimental results utilizing the above procedures were as follows.

pTRE-Luc (Clontech), one of the two regulatory components of TRES, was transfected alone or in combination with pTet-Off (ClonTech) into Sf21 cells. pTRE-Luc contains a luciferase coding region driven by the TRE-CMVmin promoter, and pTet-Off contains a tTA coding region which is driven by the full-length CMV promoter. Although the cotransfection of both components showed a slight enhancement of activity comparing to the transfection of pTRE-Luc alone, levels of stimulation were low. The luciferase activity in each experiment using the plasmids immediately above were extremely weak. These results showed that the promoter activity of full-length CMV promoter is extremely weak for producing tTA in Sf21 cells.

To utilize TRES in measuring reporting gene function in Sf21 cells, a new plasmid pAP10T was constructed as described above to replace pTet-Off. Instead of the full-length CMV promoter, a p10 promoter (Vlak et al., Virology 179:312–320, 1990; and Weyer et al., J Gen Virol 71:1525–2534, 1990) was used to drive tTA.

When increasing amounts of pTRE-Luc DNA alone were transfected into cells, luciferase activity was barely detectable. However, when various concentrations of pAP10T were cotransfected with increasing concentrations of pTRE-Luc, luciferase activity was significantly enhanced. With cotransfection of pAp10T and pTRE-Luc, the stimulation of luciferase activity was as high as 160-fold compared with pTRE-Luc transfection alone.

Luciferase activity transactivated by tTA in insect cells may have been suppressed by addition of tetracycline. Tetracycline sensitivity was evident at 0.001 µg/ml, and more than 96% of luciferase activity was suppressed at a tetracycline concentration of 0.1 µg/ml. These experiments suggest that stimulation and suppression of the TRES is highly controllable in Sf21 cells.

To determine whether the two TRES components could function in the genome of AcMNPV, pAP10T was first inserted into AcMNPV as described above. A recombinant virus, vAP10T, was subsequently produced. Luciferase activity was stimulated by coinfection of pTRE-Luc with the tTAexpressing virus, vAP10T. The greatest stimulation was observed when vAP10T was infected at an m.o.i. of 0.1. The reduced luciferase activity appearing at lower (m.o.i.=0.01) or higher (m.o.i.=1) viral concentrations were likely the results of either fewer cells being infected (lower m.o.i.) or rapid virus-induced cell death (higher m.o.i.).

The best activation ratio, a 91-fold stimulation, was observed by using pTRE-Luc at a concentration of 0.2 µg/well. The stimulation of luciferase expression, conferred by transfection of pTRE-Luc and subsequent infection with vAP10T, was inhibited by the addition of tetracycline. This inhibition exhibited repression kinetics similar to the repression conferred by the cotransfection by the two corresponding plasmid components.

The synthetic TRE-CMVmin promoter was inserted into the baculovirus transfer vector pAcUW21 as described above to yield pAPtcmL and the resulting recombinant virus vAPtcmL. Unexpectedly, once inserted into the virus, the luciferase was highly expressed with or without coinfection with vAP10T. Further treatment with tetracycline did not repress luciferase expression, suggesting that expression of luciferase from vAptcmL is not activated by the tetracycline responsive expression mechanism.

To examine the mechanism of strong luciferase expression in the TRE-CMVmin promoter-containing virus, several promoter were constructed to determine their ability to activate the luciferase gene without tTA stimulation. These promoters were the full-length CMV promoter (in pAPcL), the p10 promoter of AcMNPV (in pAP10L), the CMVmin promoter (in pAPcML), and a synthetic TRE-CMVmin promoter (in pAPtcmL). All promoters were inserted into pAcUW21, a plasmid containing lateral fragments flanking the polyhedrin gene of AcMNPV. In addition to these four constructs, PTRE-Luc (ClonTech) was used as a control.

pAPcL exhibited no promoter activity by either transfection alone or coinfection of wild type AcMNPV. The second construct, pAP10L, also exhibited no promoter activity under either condition, probably because the p10 promoter is a strong late viral promoter which requires the expression of other viral products. The third and fourth constructs, pAPcmL and pAPtcmL, had exhibited only very low promoter activity when transfected alone, but were strongly stimulated when the corresponding recombinant virus was used in coinfections. These results suggest that the CMVmin promoter, with or without a TRE element, is strongly stimulated by viral factors. However, the full-length CMV promoter was not expressed in insect cells under any condition used.

Transfer vector plasmids containing full-length CMV, TRE-CMVmin, CMVmin, and p10 promoters were used to construct recombinant AcMNPVs: vAPcL, vAPtcmL, vAPcmL, and vAP10L, respectively. The activity of several groups of independently isolated recombinant virus strains containing different promoters were tested at 72 hours post-infection at an m.o.i. of 10. The luciferase activity of all three vAPcLs was low, ranging between $1.6-2.0 \times 10^4$ RLU/µg protein, whereas the activity of the other recombinant baculoviruses containing other promoters was high. Luciferase activity of all three recombinant vAPtcmLs ranged between $3.5-3.7 \times 10^6$ RLU/µg protein. All four recombinant vAPcmLs ranged between $3.6-4.5 \times 10^6$ RLU/µg protein. A slightly higher luciferase activity using all four recombinant vAP10Ts ranged between $6.5-7.7 \times 10^6$ RLU/µg protein. These results showed that the activity of the full-length CMV promoter is approximately 200-fold lower than that of the CMVmin promoter-containing viruses.

The CMVmin promoter-containing viruses induced luciferase activity to a level similar to that expressed by the p10 promoter. Further, these results suggest that the high promoter activity exhibited by the CMVmin promoter are not limited to only some of the CMVmin promoter-containing recombinant viral isolates. Accordingly, one recombinant virus in each promoter construct was selected, and time course studies of promoter expression were performed.

The time course of promoter expression in recombinant viruses carrying different promoters was studied by examining expression of two detectable proteins: luciferase and EGFP. The activity of both proteins was first detected at 4 hours post-infection for recombinant viruses containing the CMVmin promoter (viruses vAPtcmL and vAPcmL for luciferase, and vAPtcmE for EGFP). The luciferase and EGFP activities of these viruses increased noticeably at later times and plateaued at 48 hours and 36 hours post-infection, respectively. Virus vAPcL, which contains the full-length CMV promoter, expressed luciferase approximately 200-fold less than did the vAPtcmL and vAPcmL viruses, an indication that the full-length CMV promoter is only weakly functional in the genome of AcMNPV.

The recombinant virus VAP10L, which contained the p10 promoter, behaved differently than the viruses described immediately above. The activity of the luciferase and EGFP expressed via the p10 promoter were first detected at 8 hours post-infection and reached a plateau at 48 hours post-infection or later. Although the maximal luciferase and EGFP activity expressed by the p10 promoter-containing viruses was about 2-fold (luciferase) and 16 fold higher (EGFP) than those expressed by the CMVmin promoter-containing viruses, the latter expressed luciferase or EGFP much earlier after infection.

The luciferase expressed by the CMVmin promoter-containing viruses was greater than that of vAP10L during the first 36 hours after infection. During this period, the CMVmin promoter-containing viruses expressed detectable proteins to levels similar to the same levels expressed by the p10 promoter-containing viruses, except that CMVmin-driven expression occurred 12 hours earlier than p10-driven expression.

Western blot analyses revealed that the initial detection time for luciferase and EGFP expressed from the CMVmin promoter-driven viruses vAPcmL and vAPtcmE was observed at 12 hours post-infection. In contrast, expression from p10 promoter-driven viruses vAP10L and vAP10E was observed at 24 hours post-infection. At 36 hours post-infection, the p10 and CMVmin promoter-driven viruses began to express similar amounts of their respective detectable proteins. At 72 hours post-infection, the ratio of CMVmin-driven expression to p10-driven expression was 1:1.9 for luciferase and 1:3 for EGFP.

These experiments collectively showed that the full-length CMV promoter is not functional in insect cells or in the genome of the baculovirus. However and surprisingly, the CMVmin promoter operates strongly in insect cells if delivered by viral coinfection.

What is claimed is:

1. A baculovirus comprising a DNA molecule which comprises a CMV promoter sequence and a sequence encoding an RNA, the expression of the RNA being driven by the CMV promoter sequence, wherein the CMV promoter sequence comprises SEQ ID NO:1 and is free of SEQ ID NO:2.

2. The baculovirus of claim 1, wherein the RNA is a non-baculovirus RNA.

3. The baculovirus of claim 2, wherein the RNA is a mRNA encoding a non-baculovirus protein.

4. The baculovirus of claim 3, wherein the protein is detectable.

5. A The baculovirus of claim 4, wherein the protein is luciferase.

6. A method of expressing an RNA in an insect cell, the method comprising infecting the insect cell with the baculovirus of claim 1, and expressing the RNA in the insect cell.

7. A method of expressing a non-baculovirus RNA in an insect cell, the method comprising infecting the insect cell with the baculovirus of claim 2, and expressing the non-baculovirus RNA in the insect cell.

8. A method of expressing a non-baculovirus protein in an insect cell, the method comprising infecting the insect cell with the baculovirus of claim 3, and expressing the non-baculovirus protein in the insect cell.

9. A method of expressing a protein in an insect cell, the method comprising infecting the insect cell with the baculovirus of claim 4, and expressing the protein in the insect cell.

* * * * *

SEQUENCE LISTING

```
<160> NUMBER OF SEQ ID NOS: 2

<210> SEQ ID NO 1
<211> LENGTH: 111
<212> TYPE: DNA
<213> ORGANISM: Cytomegalo virus

<400> SEQUENCE: 1
taggcgtgta cggtgggagg tctatataag cagagctcgt ttagtgaacc gtcagatcac      60
tagaagcttt attgcggtag tttatcacag ttaaattgct aacgcagtca g             111

<210> SEQ ID NO 2
<211> LENGTH: 684
<212> TYPE: DNA
<213> ORGANISM: Cytomegalo virus

<400> SEQUENCE: 2
tcaatattgg ccattagcca tattattcat tggttatata gcataaatca atattggcta      60
ttggccattg catacgttgt atctatatca taatatgtac atttatattg gctcatgtcc     120 aatgaccg   ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccctattg acgtcaatga     420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca agtctccacc ccattgacgt     600
caatgggagt ttgttttggc accaaaatca acgggacttt ccaaaatgtc gtaataaccc     660
cgccccgttg acgcaaatgg gcgg                                             684
```